(12) United States Patent
Miller

(10) Patent No.: US 9,795,495 B1
(45) Date of Patent: Oct. 24, 2017

(54) INSTRUMENTATION AND METHODS FOR KNEE ARTHROPLASTY

(71) Applicant: Timothy Ray Miller, Villa Rica, GA (US)

(72) Inventor: Timothy Ray Miller, Villa Rica, GA (US)

(*) Notice: Subject to any disclaimer, the term of this patent is extended or adjusted under 35 U.S.C. 154(b) by 18 days.

(21) Appl. No.: 14/833,186

(22) Filed: Aug. 24, 2015

Related U.S. Application Data

(60) Provisional application No. 62/041,077, filed on Aug. 23, 2014.

(51) Int. Cl.
| | | |
|---|---|---|
| *A61B 17/15* | (2006.01) | |
| *A61F 2/46* | (2006.01) | |
| *A61B 17/90* | (2006.01) | |
| *A61F 2/38* | (2006.01) | |
| *A61B 19/00* | (2006.01) | |

(52) U.S. Cl.
CPC ............ *A61F 2/4657* (2013.01); *A61B 19/50* (2013.01); *A61F 2/3859* (2013.01); *A61F 2/461* (2013.01); *A61F 2/4684* (2013.01); *A61B 2019/508* (2013.01); *A61F 2002/4658* (2013.01)

(58) Field of Classification Search
CPC ................ A61F 2/4684; A61F 2002/4668
USPC .................................... 606/88, 102
See application file for complete search history.

(56) References Cited

U.S. PATENT DOCUMENTS

| | | | | |
|---|---|---|---|---|
| 5,454,816 A * | 10/1995 | Ashby | ............... | A61B 17/155 606/102 |
| 5,486,178 A * | 1/1996 | Hodge | ............... | A61B 17/155 606/102 |
| 5,624,444 A * | 4/1997 | Wixon | ............... | A61B 17/155 606/88 |
| 5,720,752 A * | 2/1998 | Elliott | ............... | A61B 17/155 606/79 |
| 6,013,081 A * | 1/2000 | Burkinshaw | ......... | A61B 17/155 606/102 |
| 6,290,704 B1 * | 9/2001 | Burkinshaw | ......... | A61B 17/155 606/102 |
| 6,458,135 B1 * | 10/2002 | Harwin | ............... | A61B 17/155 606/88 |
| 6,916,325 B2 * | 7/2005 | Kana | ............... | A61F 2/4657 606/89 |
| 7,172,596 B2 * | 2/2007 | Coon | ............... | A61B 17/157 606/87 |
| 7,451,550 B2 * | 11/2008 | Dees, Jr. | ............ | A61B 17/1764 33/512 |
| 8,038,681 B2 * | 10/2011 | Koenemann | ......... | A61B 17/155 606/88 |
| 8,382,764 B2 * | 2/2013 | Dower | ............... | A61B 90/06 606/88 |
| 8,740,910 B2 * | 6/2014 | McMillen | ......... | A61B 17/1764 606/87 |

* cited by examiner

*Primary Examiner* — Zade Coley
(74) *Attorney, Agent, or Firm* — Whitham, Curtis & Cook, P.C.

(57) ABSTRACT

Instrumentation and methods are provided for knee arthroplasty which permit rotation of a distal femoral component in the sagittal plane. A guide provides for determination of both a femoral component size and rotation angle at which to install the implant in any specific patient.

12 Claims, 13 Drawing Sheets

INSTRUMENTATION AND METHODS FOR KNEE ARTHROPLASTY

CROSS-REFERENCE TO RELATED APPLICATIONS

This application claims the benefit of U.S. Provisional Patent Application No. 62/041,077, filed Aug. 23, 2014, the complete contents of which are herein incorporated by reference.

FIELD OF THE INVENTION

The current invention pertains to knee arthroplasty and, more particularly, instruments and methods affecting size selection and positioning of a distal femoral component for a patient.

BACKGROUND

Total knee arthroplasty involves the replacement of portions of the patella, femur, and tibia with artificial components. In particular, a proximal portion of the tibia and a distal portion of the femur are cut away (resected) and replaced with artificial components.

The femoral component is generally a metallic alloy construction (e.g. cobalt-chrome alloy or 6A14V titanium alloy) and provides medial and lateral condylar bearing surfaces of multi-radius design of similar shape and geometry as the natural distal femur or femoral-side of the knee joint.

FIG. 1A is an example of a standard femoral component 7. The interior of the component has five planar fixation surfaces 1-5 and may also include an intramedullary ("IM") stem 6. Prior to installation of the component 7, the distal femur must be prepared so that it has five fixation surfaces which match the interior surfaces of the component. More particularly, and with reference to FIG. 1B, a distal femur 8 must be resected to have a distal cut surface 1' (corresponding to surface 1 in FIG. 1A), a posterior cut surface 2' (corresponding to surface 2 in FIG. 1A), an anterior cut surface 3' (corresponding to surface 3 in FIG. 1A), an anterior chamfer cut surface 4' (corresponding to surface 4 in FIG. 1A) and a posterior chamfer cut surface 5' (corresponding to surface 5 in FIG. 1A). These cuts are typically made with oscillating saw blades. In scenarios where additional stability is desired, the IM canal of the distal femur 8 may be reamed to accept an IM stem 6 of a femoral component 7. A femoral component without an IM stem may also be used.

A femoral component may be located with six degrees of freedom relative to the patient's femoral geometry. These may be expressed in a Cartesian manner relative to orthogonal anatomical reference planes as shown in FIG. 2. There are three types of angulation/rotation, namely varus-valgus angulation, flexion-extension angulation, and internal-external rotation. Additionally, there are three types of linear position, namely inferior-superior, anterior-posterior and medial-lateral. It should be noted that the joint shown in FIG. 2 is rotated into flexion. As a result, the anterior and posterior sides of the distal femur are not arranged along the antero-posterior position axis. To position a distal femoral component on the bone, a number of datum features of a patient's anatomy and their relative location as controlled by soft tissue structures at the knee may be utilized.

A goal of total knee arthroplasty is to resect the damaged bone on the distal femur and replace it with the same amount (e.g., volume) of material (e.g. metal of the distal femoral component implant) as the normal undamaged bone that was there prior to damage, thus restoring normal ligament tension and kinematics (motion) to the repaired joint. Current and historical instrumentation techniques resect the distal femur perpendicular to the femoral mechanical and longitudinal (anatomic) axis in the sagittal plane. FIG. 1B shows the typical 90 degree angle of the distal cut surface 1' with respect to the longitudinal axis 9. Conventionally, the distal cut is the first resection to be made, the remaining four cuts (i.e. anterior, posterior, anterior chamfer, and posterior chamfer) typically being made with respect to the distal cut surface 1' after it has been prepared.

In ideal circumstances, a femoral component exists with a femoral component size which exactly matches the specific femur size for any given patient. FIG. 3A shows an ideally sized femoral component 30 fitted on a distal femur. In this scenario, the posterior flange 12 of the femoral component replaces the posterior resected bone with the same amount of metal and the anterior flange 13 of the femoral component is flush with the anterior femur.

An issue arises when no femoral component size exactly matches the distal femur size of a specific patient. Femoral components are traditionally made in "stock" or standardized sizes. The "ideal" fit illustrated in FIG. 3A is generally not attainable with stock femoral component sizes which are not optimized for specific patients. A finite number of sizes are produced by the manufacturer and a specific patient is fitted with whichever available stock femoral component size is closest to the unique distal femur size of that specific patient. As a rough analogy, comparison may be made to pant sizes at a department store, where a limited number of sizes are offered according to standardized waist and inseam measures. A "perfect" fitting pair of pants would be made from raw textiles which are measured, cut, and sewn by a tailor for a specific individual. Producing custom femoral components in knee arthroplasty is cost prohibitive, and thus the practice of selecting the closest fitting femoral component size from a finite selection of sizes remains the industry standard.

There are two approaches on how to accommodate the issue of an inexact match between the sizes of available stock femoral components and the unique distal femur size of a specific patient.

The first approach is called "anterior referencing", where the anterior cut for the femoral component is made at the normal position in order to avoid notching the femoral bone on the anterior side and potentially lead to future femoral fracture. In reference to FIG. 1B, anterior referencing provides anterior cut surface 3' such that the amount of anterior bone resected substantially matches the volume of the anterior flange 13 of the femoral component 7. In order to permit the knee to rotate into flexion if the size of the patient-specific femur is between the standard femoral component sizes, the surgeon undersizes the femoral component. As an illustrative example, consider a scenario where there is a standard femoral component size "M" and a standard femoral component size "S", where "S" is the closest available size to "M" that is also smaller than "M". If "M" is larger than the patient-specific femoral size and "S" is smaller than the patient-specific femoral size, the surgeon selects the femoral component of size "S" for implanting in the specific patient in question. Undersizing in this manner requires cutting more posterior bone for posterior cut surface 2' (FIG. 1B) than is replaced with femoral component material (e.g., metal). This causes an abnormal looseness of ligaments in flexion and possible clinical issues or implant longevity issues.

The other approach is called "posterior referencing". In this case, the amount of posterior bone resected substantially matches the volume of the posterior flange 12 (FIG. 1A) of the femoral component 7 so there is no compromise in the ligament tension when in the knee is in flexion, thereby restoring the ligament balance to more normal conditions. If the patient-specific femur is between the stock femoral component sizes, the common practice is upsizing in order to prevent notching the anterior femur which can potentially cause fracture of the bone post operatively. However, upsizing causes an overstuffing of the patellofemoral space and can lead to limited motion, fracture of the patellar bone, or failure of the patella implant.

In order to minimize the potential operative and post-operative issues with each of the above two approaches, manufacturers have added additional stock sizes of femoral components thereby reducing the difference between stock femoral component sizes. This practice adds cost to the procedure and the industry in general.

FIGS. 3B and 3C show, respectively, an undersized femoral component and an oversized femoral component in traditional alignment, e.g., the distal resection has been made 90 degrees with respect to the longitudinal axis 9 of the femur. In other words, distal cut surface 1' is orthogonal to the longitudinal axis 9 (see FIG. 1B). As shown, the undersized femoral component 31 and the oversized femoral component 32 are arranged with posterior referencing. FIG. 3B shows that to accommodate an undersized femoral component 31, the end of the anterior cut surface 3' notches the anterior femur. In the alternative that the undersized femoral component 31 is moved to an anterior referencing position (still according to a traditional orthogonal alignment), more bone would be resected posteriorly than would be replaced with the femoral component's posterior flange. FIG. 3C shows how an oversized femoral component 32 may cause the anterior flange 13 of the component to be spaced from an anterior surface of the femur where the anterior flange terminates (i.e. the proximal end of the anterior flange 13).

SUMMARY

The proposed system alleviates the compromises of the traditional anterior referencing and posterior referencing systems by providing an instrumented method to rotate the distal femoral cut in the sagittal plane. Rotation of the distal femoral cut in the sagittal plane replaces the standard 90 degree cut and may allow the same amount of resected posterior bone to be replaced by the femoral component. Yet, in sharp contrast to traditional posterior referencing, rotation of the distal femoral cut in the sagittal plane may eliminate the risk of notching the anterior femur by adjusting the angle of the anterior cut relative to the anterior surface of the femur. This permits a reduced number of stock femoral component sizes without making the compromises of known systems. It would also allow a smaller number of components to be taken into the operation room (OR) for a specific surgery.

An advantage which may be realized with exemplary embodiments of the invention is a reduction in the total number of unique femoral component sizes which must be manufactured and stocked in order to cover a large number of patients presenting a wide range of individual femur sizes. For reasons such as material cost and manufacturing complexity, the cost of individual femoral components is very expensive. Thus, the more component sizes necessary to manufacture and stock, the greater the overhead costs to companies and/or hospitals. There can also be greater losses if, for example, a particular make or model of femoral component becomes obsolete or recalled. The financial ramifications are higher the greater the number of femoral component sizes and therefore individual femoral components that are produced or stocked.

Conventionally, a single implant company produces a line of femoral components from a smallest size to a largest size. The line may include, for example, 14 different femoral component sizes. This results in a total of 28 unique femoral components, 2 at each femoral component size, due to the fact that a femoral component for the left knee and a femoral component for the right knee require small differences in their overall geometry.

According to an exemplary embodiment of the invention, a complete line of femoral components is provided where each component size is useable with a larger range of actual patient femur sizes without significant compromise to the patient's post-operative range of motion and kinematics with the implant as compared to the pre-operative range of motion and kinematics with a healthy knee. In short, the maximum difference between any given patient's femur size and the determined femoral component size for that patient may be greater as compared to conventional systems, and yet this may be accomplished without overstuffing the patellofemoral space, removing more bone from the posterior femur than is replaced with the component (e.g. the posterior flange of the component), or notching the anterior femur.

As an example, a particular sample of patients may include a patient with a femur size of 50 mm and another patient with a femur size of 56 mm, all other patients having femur sizes falling between these two sizes. To cover this actual femur size range of 6 mm, a prior art product line may require at least two different femoral component sizes: a size 'X' for actual femur sizes 50 mm-52.9 mm and a size 'Y' for actual femur sizes 53 mm-56 mm. In contrast, a product line or system according to an exemplary embodiment of the invention may use just the single size 'Y' (or, alternatively, a single size 'A') for actual femur sizes 50-56 mm.

Product lines or systems according to exemplary embodiments of the invention can effectively cover ranges of actual femur sizes equal to or greater than prior art product lines/systems but with fewer femoral component sizes. For example, instead of requiring 14 femoral component sizes and thus 28 different components, 10, 9, 8, 7, 6, 5, or even fewer femoral component sizes may be produced and utilized, requiring as a result only 20, 18, 16, 14, 12, 10, or even fewer femoral components, respectively.

Fewer femoral component sizes and thus fewer different components for a complete product line means fewer components need to be purchased and/or stocked, be it by a company or hospital. Conventionally over the past two decades, the manufacturing company kept an inventory, be it at their own premises or on hospital property. For every individual patient case, a company representative would bring in a selection of the sizes from the full range as options for the surgeon to use with that particular patient. In recent years, a growing trend has been for hospitals to purchase the inventory up front, leading to higher costs for hospitals. A reduction in the total number of femoral component sizes and thus different femoral components which must be stocked by either a company or hospital as is possible with the present invention is therefore particularly advantageous.

At the time of surgery, it is also typical for a surgeon to bring more than one femoral component size into the operating room (OR). During the surgery, the surgeon then has flexibility in selecting which size to ultimately install on the patient's femur, whether or not pre-operative planning was conducted to select a size as the most likely candidate.

In exemplary embodiments of the invention, a surgeon can bring into the OR a group of components covering the same or a greater range of actual femoral component sizes as with a prior art system, yet the group of components can be fewer in number as compared to the prior art.

As one example, assume that according to a conventional system there is a 2.75 mm difference between each femoral component size from smallest to largest. For the surgeon to have the flexibility of having an appropriate component for any actual femur size within a certain 15 mm range, the surgeon must normally take in 6 components. In contrast, according to an exemplary embodiment of the invention, the surgeon desiring the same flexibility may take in fewer than 6 components, e.g. 3 components with a 5 mm difference between each femoral component size from smallest to largest.

As another example, assume that according to another conventional system there is a 2 mm difference between each femoral component size from smallest to largest. For the surgeon to have the flexibility of having a suitable component for any actual femur size within a range of 15 mm, the surgeon must normally take in 8 components into the OR. In contrast, according to an exemplary embodiment of the invention, the surgeon desiring the same flexibility may take in fewer than 8 components, e.g. 4 components with a 4 mm difference between each femoral component size from smallest to largest or, alternatively, 3 components with a 5 mm difference between each femoral component size from smallest to largest.

As yet one further example, assume that according to still another conventional system there is a 2 mm difference between each femoral component size from smallest to largest. For the surgeon to have the flexibility of having a suitable component for any actual femur size within a certain 10 mm range, the surgeon must normally take 5 components into the OR. In contrast, according to an exemplary embodiment of the invention, the surgeon desiring the same flexibility may take in fewer than 5 components, e.g. as few as 2 components with a 5 mm difference between the two femoral component sizes.

According to an aspect of the invention, a method is provided for performing knee arthroplasty procedures in a hospital setting. The method includes using a femoral component of a selected size on patients with differing sized femurs by, on a patient by patient basis, (i) determining an angle relative to a datum feature of a specific patient's femur at which to install the femoral component, the angle at which to install the femoral component being variable from patient to patient, and (ii) installing the femoral component of the selected size on the specific patient's femur at the angle determined in the determining step. In some embodiments, the determining step is performed with an instrumented guide which is rotatable about an end of the specific patient's femur. In other embodiments, the determining step is performed using one or more computer-generated models which take as input medical images of the specific patient's femur. The method can include the step of determining the selected size of the femoral component.

DETAILED DESCRIPTION

As used herein, when referring to bones, other body parts, or implant components in the implanted position, the term "proximal" means closest to the heart and the term "distal" means more distant from the heart. When referring to tools and instruments, the term "proximal" means closest to the practitioner (e.g., surgeon) and the term "distal" means distant from the practitioner.

As used herein, "distal femur" refers to the distal end portion of the femur from at least where the shaft ends to the most distal point on the femur. This includes both the medial and lateral condyles. Meanwhile, "anterior femur" may be used in reference to the anterior side of the distal femur. Similarly, "posterior femur" may be used in reference to the posterior side of the distal femur. "Distal end" may be used in reference to the most distal surface of the femur, e.g. that which is removed by the distal cut when performing a total knee arthroscopy (TKA).

Figure 1A:
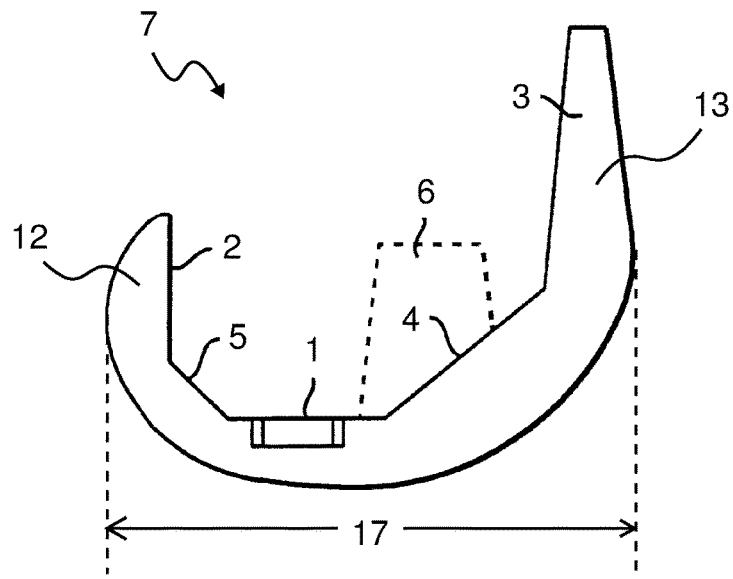
FIG. 1A is a distal femoral component.
Figure 1B:
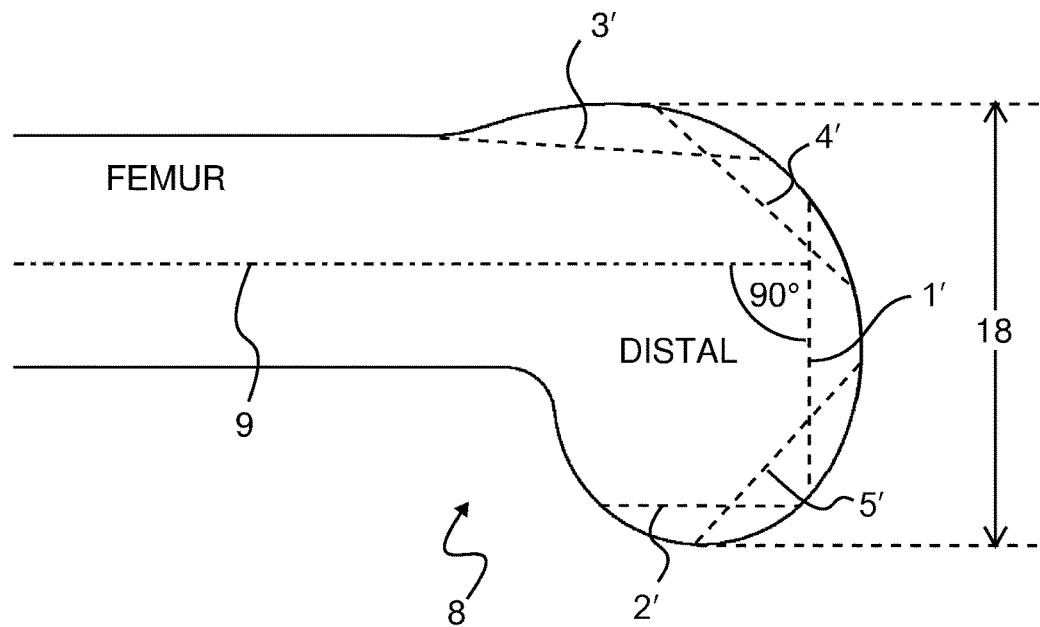
FIG. 1B is a schematic of a distal femur showing cut surfaces for knee arthroplasty.
Figure 2:
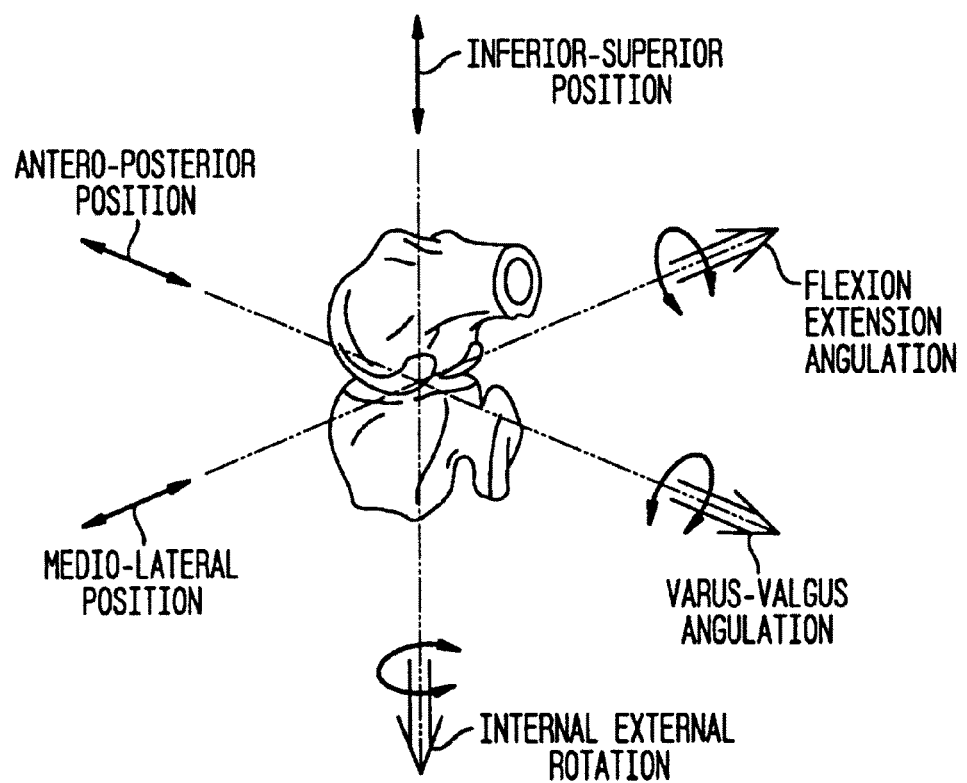
FIG. 2 shows six degrees of freedom usable to describe the orientation of a femoral component with respect to femoral geometry.

Generally, "femoral component size" 17 as used herein refers to the maximum distance between a posterior flange 12 and an anterior flange 13 as indicated in FIG. 1A. This is a measurement in the anterior-posterior direction. Similarly, "femur size" 18 will generally refer to anterior-posterior (AP) size, or the maximum distance between the most prominent portion of the anterior surface of the distal femur and the most prominent posterior surface of the medial or lateral condyle as indicated in FIG. 1B, unless otherwise specified. These definitions are not intended to be limiting, and other sizing definitions may occur to those of skill in the art and be likewise applicable with the teachings herein.

Figure 3A:
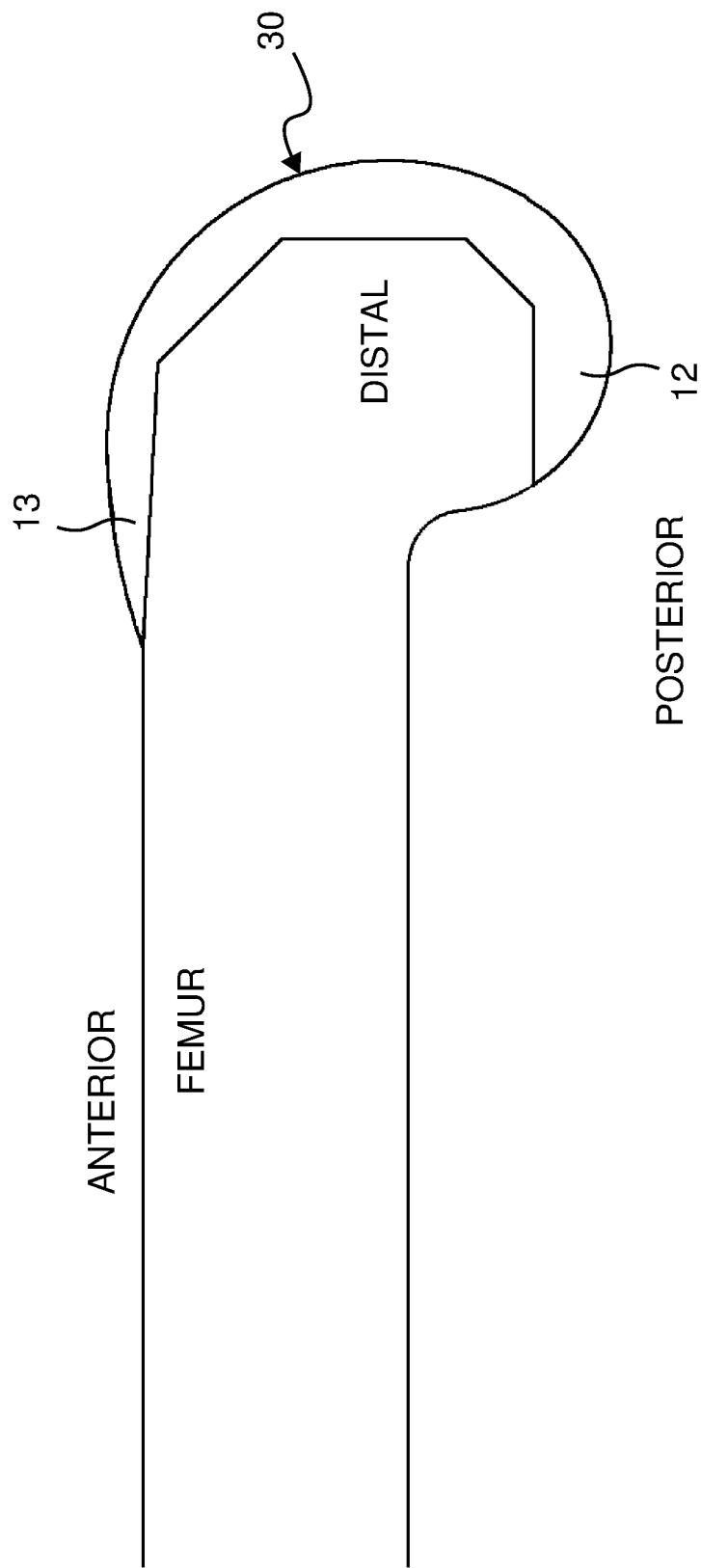
FIG. 3A is a schematic showing an ideal femoral component fit on a distal femur, where femoral component size matches distal femur size in the anterior-posterior direction.
Figure 3B:
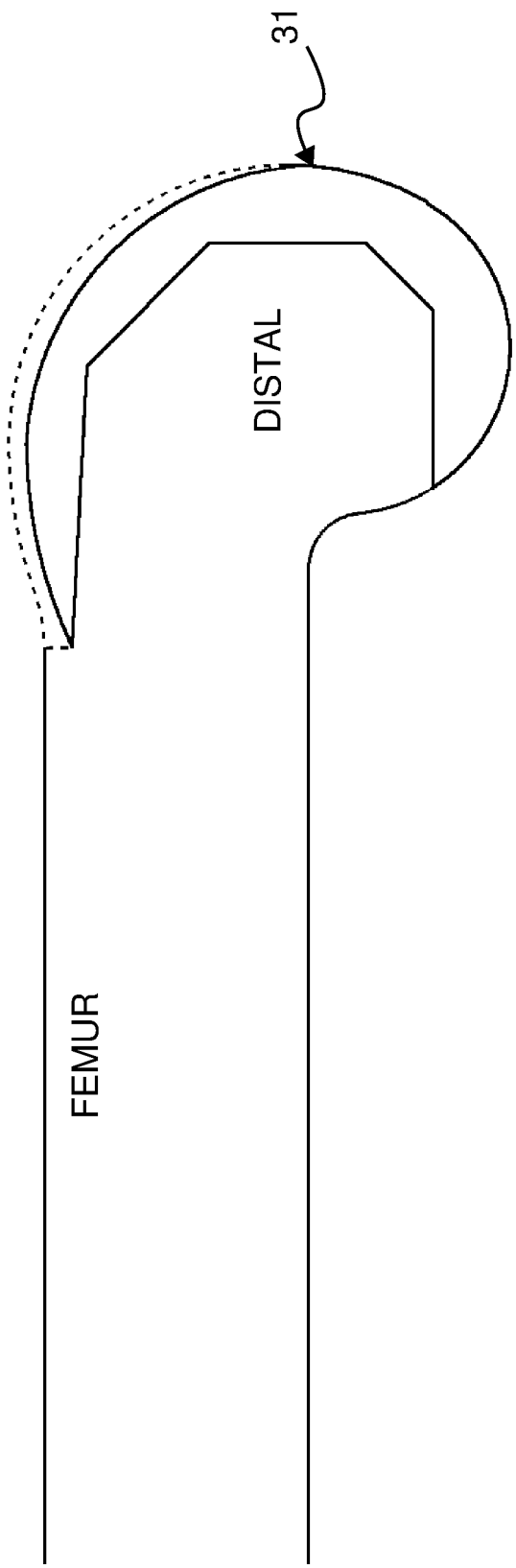
FIG. 3B is a schematic showing an undersized femoral component with posterior referencing in a traditional alignment.
Figure 3C:
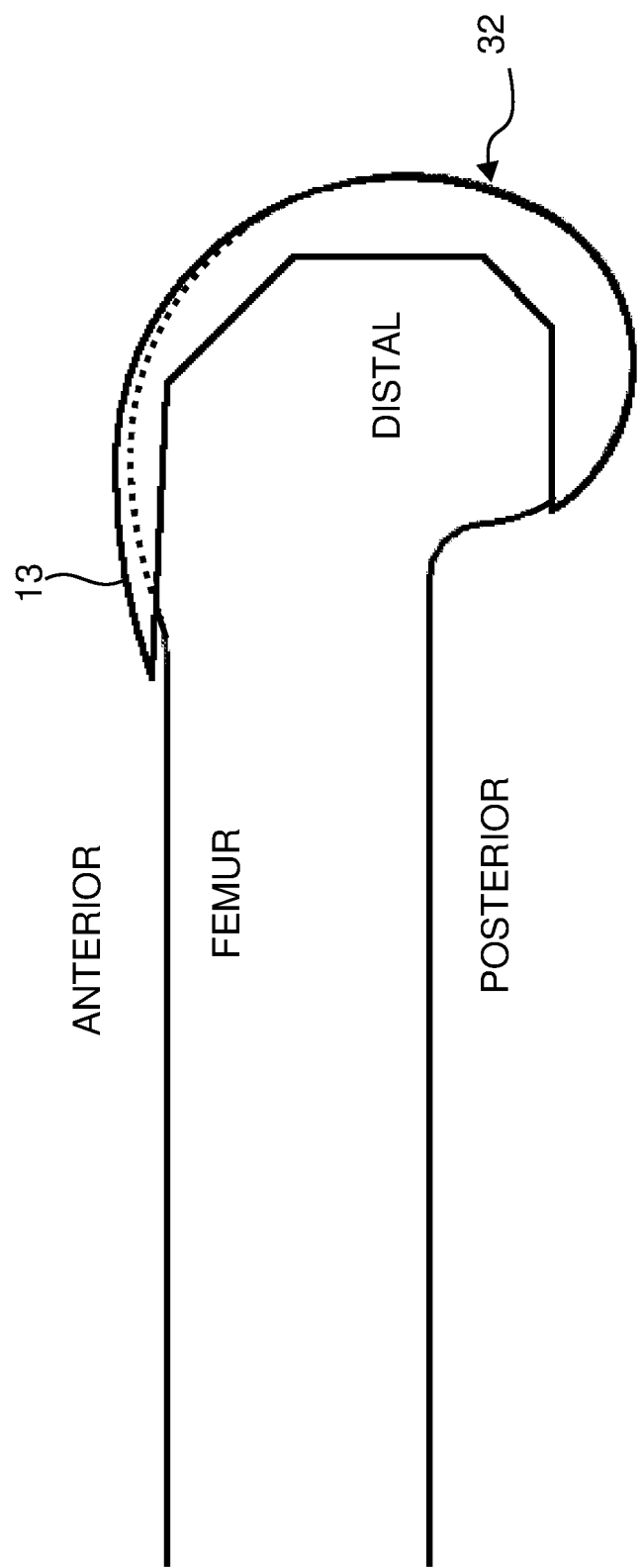
FIG. 3C is a schematic showing an oversized femoral component with posterior referencing in a traditional alignment.
Figure 4:
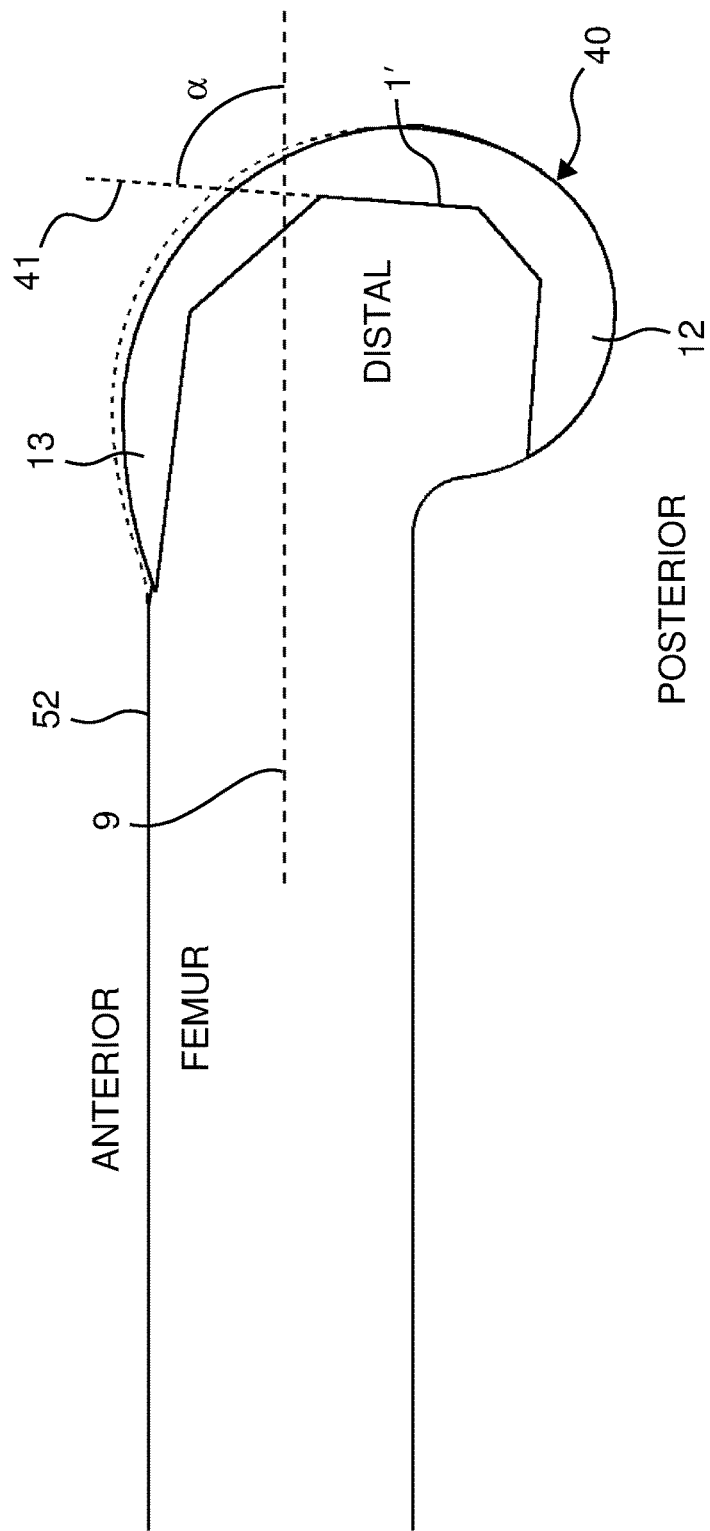
FIG. 4 is a schematic of an undersized femoral component rotated into a flexed position.

FIG. 4 shows a distal femoral component 40 installed on a distal femur according to an exemplary embodiment of the invention. Absent a stock femoral component size which matches the size of a patient-specific femur, an undersized femoral component is selected for use. However, in contrast to the traditional alignment whereby the distal resection is made orthogonal to the longitudinal axis 9, an angle α between the longitudinal axis 9 and the distal resection plane 41 is less than 90 degrees (as measured in a sagittal plane of the femur). The distal cut surface 1' is not made orthogonal to the longitudinal axis 9 but rather has a rotated angle of (90-α) degrees. More specifically, this rotation is in the direction of flexion in the sagittal plane. The angle of rotation may be, for example, an angle above 0 degrees up to 10 degrees. As another alternative, the angle of rotation may be, for example, an angle above 0 degrees and up to 8 degrees. As still another alternative, the angle of rotation may be, for example, an angle above 0 degrees and up to 6 degrees. In addition, posterior referencing may be used in exemplary embodiments. The amount of resected bone may be less than the amount if the distal cut was made at 90 degrees as depicted in FIG. 3B. The amount of bone removed from the posterior femur is preferably replaced by a substantially equal amount of component material of the posterior flange 12, and the anterior femur has either no notch or a reduced notch as compared to, for example, that shown in FIG. 3B in the bone at the (proximal) end of the anterior flange 13. In some exemplary embodiments, the proximal end of the anterior flange 13 is flush with a natural (uncut) surface 52 of the anterior femur.

For a given patient, the problem arises of determining both an appropriate femoral component size from a finite number of stock femoral component sizes as well as an angle with which to install a femoral component having the femoral component size such that the combination of selected size and angle of rotation in flexion have the benefits discussed in the preceding paragraph.

Figures 5A, 5B:
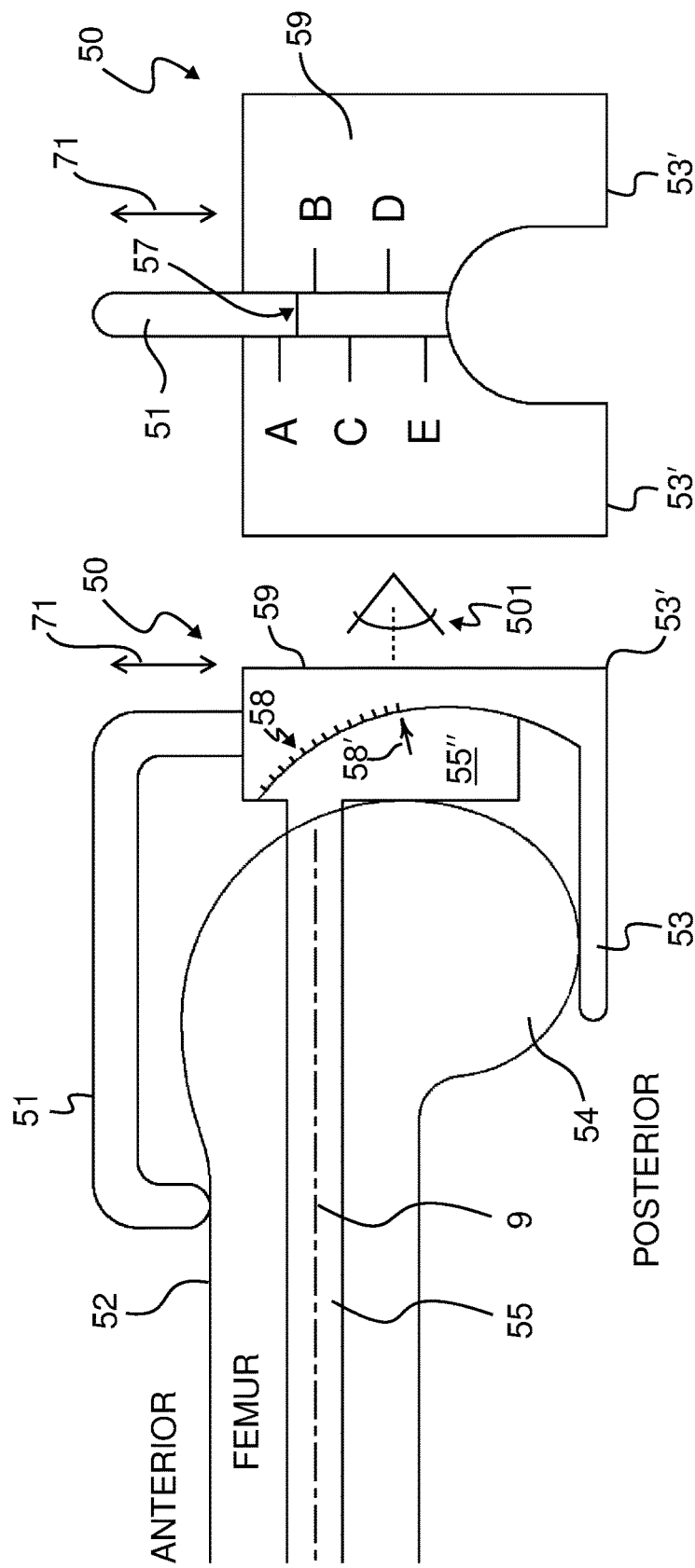
FIGS. 5A and 5B are views of a guide for determining a femoral component size and angle at which to install a femoral component having the femoral component size.

FIGS. 5A and 5B are views of a schematic representation including an exemplary guide 50 that permits a determination of both a femoral component size and an angle at which to install a femoral component having the femoral component size. The guide 50 is useable to determine the pairing of a femoral component size and angle for each of a plurality of different patients, where each patient may have a different femur size. A single guide 50 may be usable with the entire spectrum of femur component sizes of humans (especially adult humans) and/or the entire spectrum of femur component sizes for a particular species of animal (e.g. horses or dogs).

A guide 50 for determining or selecting a size and positioning of a femoral component for knee arthroplasty of a patient-specific femur (characterized by, e.g., a longitudinal axis, an anterior surface, and a posterior surface) generally comprises an alignment mechanism for aligning the guide 50 with the a datum feature (e.g., longitudinal axis 9) of the femur, an anterior referencing part that contacts the anterior surface, and a posterior referencing part that contacts the posterior surface. Generally, a guide 50 also comprises a pointer and a plurality of sizing indicia, where at least one of the pointer and the plurality of sizing indicia is moveable with respect to the other when either or both the anterior referencing part and the posterior referencing part are rotated in a sagittal plane of the patient-specific femur relative to the alignment guide. During a rotation, the anterior referencing part maintains contact with the anterior surface of the femur, and the posterior referencing part maintains contact with the posterior surface of the femur. Note that the sizing indicia may take a variety of forms. While lines and letters are used for purposes of illustration in the drawings, sizing indicia may be, for example, hash marks, numbers, indents, or other markings or indicators where each respectively corresponds with an individual stock femoral component size available to the surgeon for use on a patient.

According to the exemplary embodiment in FIGS. 5A and 5B, the anterior referencing part may be a stylus 51 which preferably maintains contact with an anterior surface 52 of the femur which is proximal to the condyles of the femur. The posterior referencing part may be one or more feet 53 which preferably maintain contact with one or more posterior surfaces of condyles 54 of the femur. The alignment mechanism may be, for example, an intramedullary (IM) guide 55 inserted into the IM canal of the femur. Alternatively, the alignment mechanism may simply be fixable to an IM rod which is inserted into the IM canal. Other alignment mechanisms may also occur to those of skill in the art and be used in accordance with the invention.

In an exemplary embodiment, the pointer may consist of or include a marker 57 on a portion of the stylus 51. The plurality of sizing indicia, shown in FIG. 5B as letters 'A' through 'E', may be arranged on a portion 59 of the guide 50. Each indicium corresponds with one femoral component size of a plurality of available femoral component sizes. Thus, in this example, there would be five femoral component sizes with 'A' as the largest available size, 'E' as the smallest available size, and 'B' through 'D' as intermediate sizes at regular intervals therebetween. Body 59 of the guide may be connected to or integrally formed with the one or more feet 53 at edge 53'. For example, the feet 53 may be extensions or protrusions from the body 59. Additionally, body 59 may include or attach to the alignment mechanism (e.g., IM guide 55) such as is shown in FIG. 5A.

The anterior referencing part (e.g., stylus 51), the posterior referencing part (e.g., feet 53), body (e.g., body 59), and the alignment mechanism (e.g., IM guide 55) may be connected such that a rotation of one or more of the anterior referencing part, the posterior referencing part, and the body are rotatable with respect to the alignment mechanism and thereby with respect to a datum feature of the femur (e.g., longitudinal axis 9). In an exemplary embodiment, the stylus 51, foot or feet 53, and body 59 are all rotatable together with respect to the alignment mechanism.

Use of a guide 50 as part of a knee arthroplasty procedure will be described in connection with FIGS. 5A-5B, 6, 7A-7B, and 8A-8B. After the distal femur has been accessed and prepared in accordance with operating procedures known in the art, the alignment mechanism of guide 50 should be arranged for identifying and maintaining a relative position to a datum feature of the femur. The datum feature may be, for example, the femoral shaft or the line joining the center of the knee and the hip joints. Two major techniques for accomplishing this are currently used. First is intramedullary alignment. A rod is introduced through the center of the knee into the intramedullary space and passed up the inside of the femur to the internal isthmus, establishing an instrument axis within the femoral shaft (medullary canal of the femur). This technique has been found to be very reliable. The second is extramedullary alignment. An external guide rod is aligned with the anterior cortex of the femur, or from the center of the knee to the femoral head.

Figure 6:
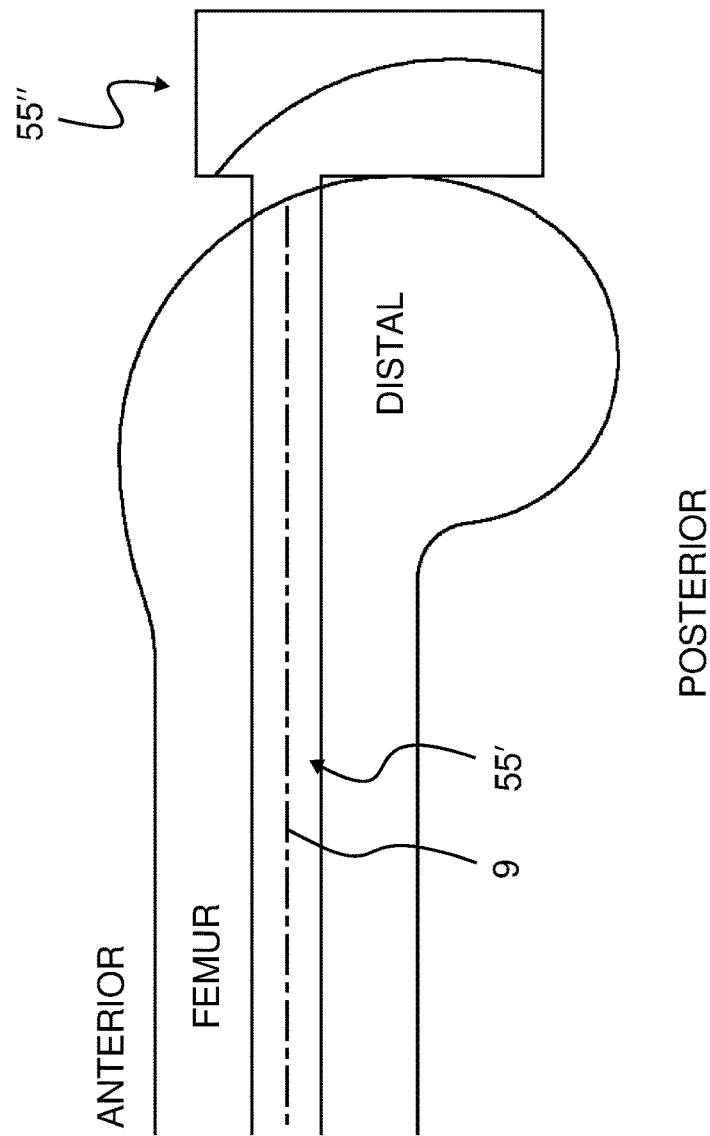
FIG. 6 is a schematic of an intramedullary (IM) guide installed on a femur.

FIG. 6 shows an exemplary alignment mechanism which provides intramedullary (IM) alignment. In this case, the alignment mechanism is an intramedullary (IM) guide 55 which may include a rod portion 55' and a head portion 55" to which additional components of the guide 50 are attached or attachable. The IM guide 55 may be inserted into the femoral shaft until the head portion 55" is in contact with the distal end of the femur.

Proper arrangement of the alignment mechanism fixes the alignment mechanism's position and orientation with respect the femur. In an exemplary embodiment, the alignment mechanism has a fixed positioned and orientation with respect to a longitudinal axis 9 of the femur. With the alignment mechanism in place, the remainder of the guide 50 may be connected thereto. In some embodiments, the alignment mechanism may not be fully separable from the other components of the guide 50, in which case arranging the alignment mechanism may automatically arrange the full guide 50, e.g., according to FIGS. 5A and 5B. With the guide 50 arranged on the femur, it is beneficial to ensure that the anterior referencing part and the posterior referencing part are in contact with the appropriate contact points of the femur. The stylus 51 is preferably in contact with and thus determines a location of anterior surface 52 of the femur, and the two feet 53 are in contact with and thus determine locations of the outermost contact points of the posterior surfaces of condyles 54.

FIGS. 5A and 5B shows the guide 50 in a starting position whereby the angle of installation provided by the guide is 0 degrees. This implies that there is 0 degrees of rotation from an orthogonal direction with respect to the longitudinal axis 9. For most patients, the guide 50 will not yet provide a determination of a femoral component size to use. This would only occur if a femoral component size exists which exactly matches the actual femur size of the patient. For the majority of patients, the exact femur size of the patient will fall somewhere between two stock femoral component sizes. As a result, the pointer 57 will fall between two consecutive sizing indicia. In FIG. 5B, the pointer 57 is in between sizes 'A' and 'B'.

Figures 7A, 7B:
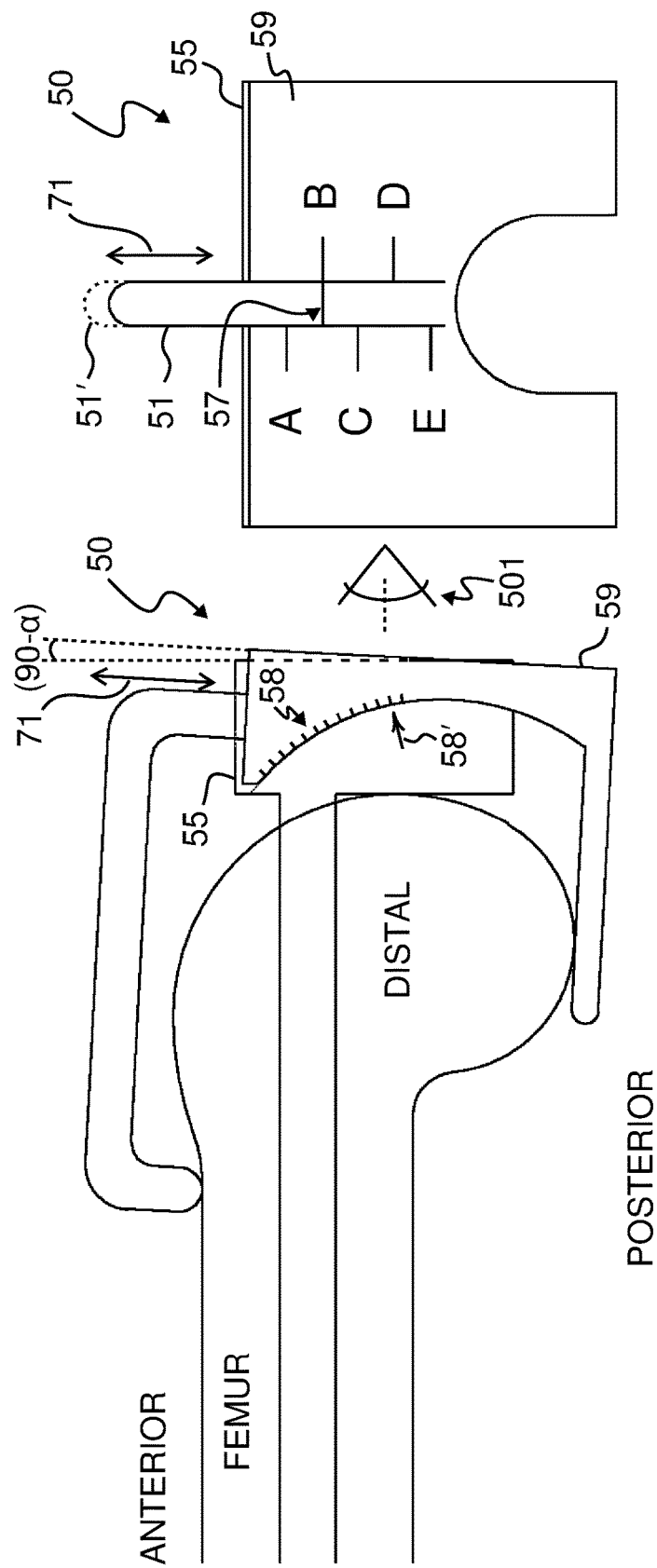
FIGS. 7A and 7B are views of the guide of FIGS. 5A and 5B rotated into flexion.

When the pointer does not indicate a specific sizing indicium and thus a specific available femoral component size when the guide is arranged at 0 degrees, the guide 50 should be rotated into flexion until the pointer 57 aligns with the next/nearest sizing indicium. Such a rotation is shown in FIGS. 7A and 7B. According to exemplary embodiments, a stylus 51 is connected to the body 59 such that the stylus can slide along a displacement axis 71. Movement of the stylus 51 along axis 71 changes a spacing of the stylus 51 with respect to the foot or feet 53, thereby permitting the stylus to maintain contact with the anterior surface 52. FIG. 7B shows the starting height 51' of the stylus 51 (corresponding with the height in FIG. 5B) in dashed lines and the reduced height subsequent to the rotation in solid lines. The reduction of the spacing between the stylus 51 and the feet 53 along the displacement axis 71 permits the alignment of the pointer 57 with a sizing indicium, in this example sizing indicium 'B'.

Once the pointer 57 and a sizing indicium are aligned, the angle for installing a femoral component having the size indicated by the aligned sizing indicium is provided by the guide. This may be obtained, for example, by the relative positions of angle indicia 58 and 58' which move relative to one another during rotation.

As previously stated, an exemplary guide 50 permits determination of both a femoral component size and an angle of rotation in a sagittal plane of the femur at which to install the femoral component having the determined femoral component size. The size and angle may be determined simultaneously and will typically differ from one patient to another. Furthermore, while it may be determined that two patients require the same femoral component size, a different angle may be determined for each patient. Conversely, while it may be determined that two patients require the same angle, a different femoral component size may be determined for each patient.

The angle of installation in the sagittal plane will vary based on the difference between the patient's true femoral size and the size of the femoral component implant. For example, if the patient has a 51 mm femoral size, the guide may determine the patient should receive a 50 mm component. In this case, the angle would be a first value of X degrees. If a second patient's femoral size is 54 mm but the guide determines the second patient should also receive a 50 mm component, the guide will determine that the angle for the second patient should be a second value of Y degrees, where Y>X. A rotation of the guide (or more specifically a rotation of a rotatable element of the guide with respect to a stationary element of the guide) will be greater with the 54 mm patient than with the 51 mm patient to ensure the anterior cut surface for the anterior flange of the femoral component does not notch the femur. Thus despite the same size femoral component being used in both patients, the component is rotated more or less depending on the difference between the actual patient femoral size and the component size.

Figure 9:
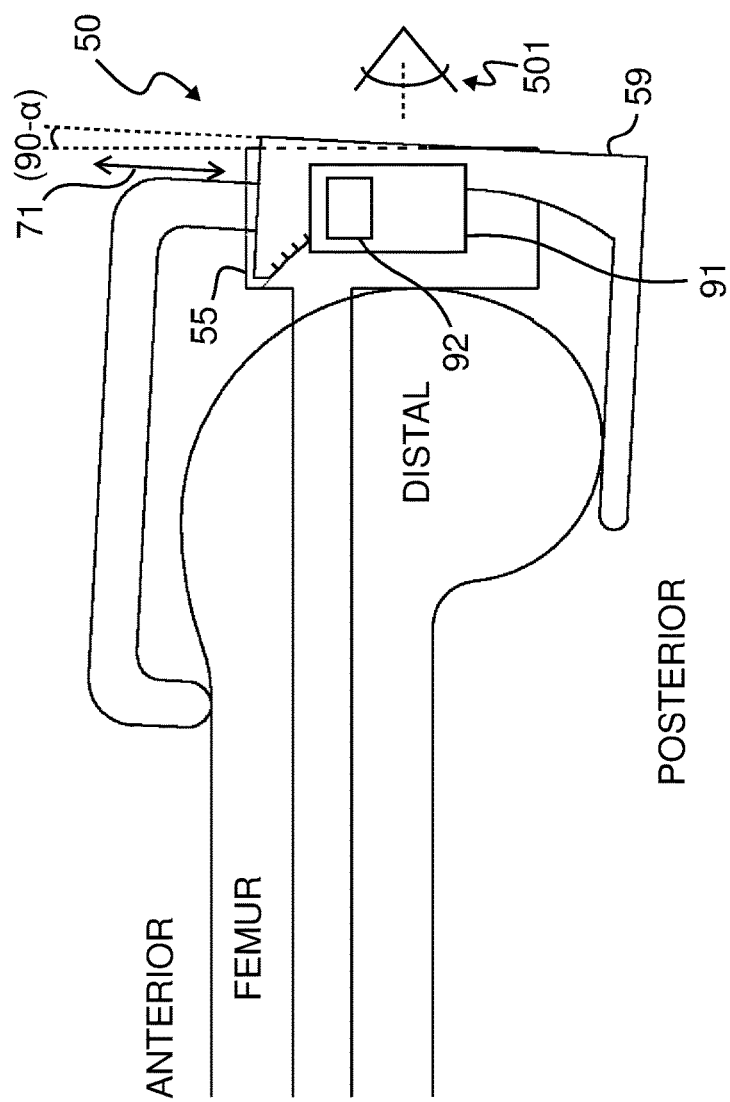
FIG. 9 shows a guide that includes an electronic gauge for determining femoral component size and installation angle.

Different exemplary embodiments of the invention may provide different means by which the femoral component size and angle of rotation may be read from the guide. According to the exemplary embodiment of FIGS. 5A-5B and 7A-7B, the available femoral component sizes are given by indicia (e.g., 'A' through 'E') on the guide 50, and the angle for installing the femoral component is given by or may be calculated from the relative positions of angle indicia (e.g., angle indicia 58 and 58' on the portion 59 and head 55" of the alignment mechanism (IM rod 55)). FIGS. 5A and 7A show the femur and guide 50 as viewed facing a (median-) sagittal plane of the femur. FIGS. 5B and 7B are views of the same setups but viewed from the direction indicated by symbol 501. FIG. 9 shows an alternative embodiment in which a guide 50' includes an electronic gauge 91, illustrated schematically. Components which are substantially the same between guides 50 and 50' are labeled with the same reference numerals. Some embodiments may combine both an electronic gauge 91 and physical indicia (e.g., sizing indicia A-E and indicia 57, 58, and 58') as provided with guide 50. Other embodiments may include the electronic gauge 91 in place of physical indicia. The electronic gauge 91 detects the position of the posterior referencing part relative to the anterior referencing part of guide 50' (e.g., the spacing between the posterior referencing part and the anterior referencing part before and after the rotation in the sagittal plane). The electronic gauge determines/selects a femoral component size for the patient-specific femur based on the detected position. The electronic gauge identifies the closest femoral component size match available as the surgeon rotates the guide 50' into flexion. The electronic gauge 91 includes an output device such as display 92 (e.g., a LCD display) which shows the selected stock femoral component size. As was the case with guide 50, a rotation of either or both the anterior and posterior referencing parts relative to the alignment mechanism determines an angle relative to the datum feature at which to install a femoral component having the selected femoral component size on the patient-specific femur. In some embodiments, the electronic gauge 91 makes this determination by detecting the position of the alignment mechanism relative to the anterior referencing part or the posterior referencing part. The determined angle is then displayed on display 92. The output device of the electronic gauge 91 can consist of or include a wireless or wired link to transmit the size and/or angle determined for a specific patient femur to an external computer or display.

Subsequent to a determination of the femoral component size and angle at which to install the implant in the sagittal plane, the distal resection of the femur may be made at the determined angle. As shown schematically in FIGS. 8A and 8B, the resection may be performed using an adjustable cutting block 81 configurable to resect the distal end of a femur at an angle in the sagittal plane which is either orthogonal or non-orthogonal to the longitudinal axis 9 of the femur. Specifically, the distal cutting block should be arranged to permit a resection of the distal femur at the angle of installation (or near the angle) determined from the guide 50. In exemplary embodiments, this has the effect of giving a distal cut surface 1' at an angle (90-α) into flexion as discussed above with respect to FIG. 4. It should be noted that resection of the distal end of the femur at a particular angle and installation of the femoral component at a particular angle may be understood to include a margin of error or a certain tolerance. For example, a distal resection may be made and the distal component may be installed at the angle given by the guide 50 plus or minus 0.5 degrees.

Figure 8A:
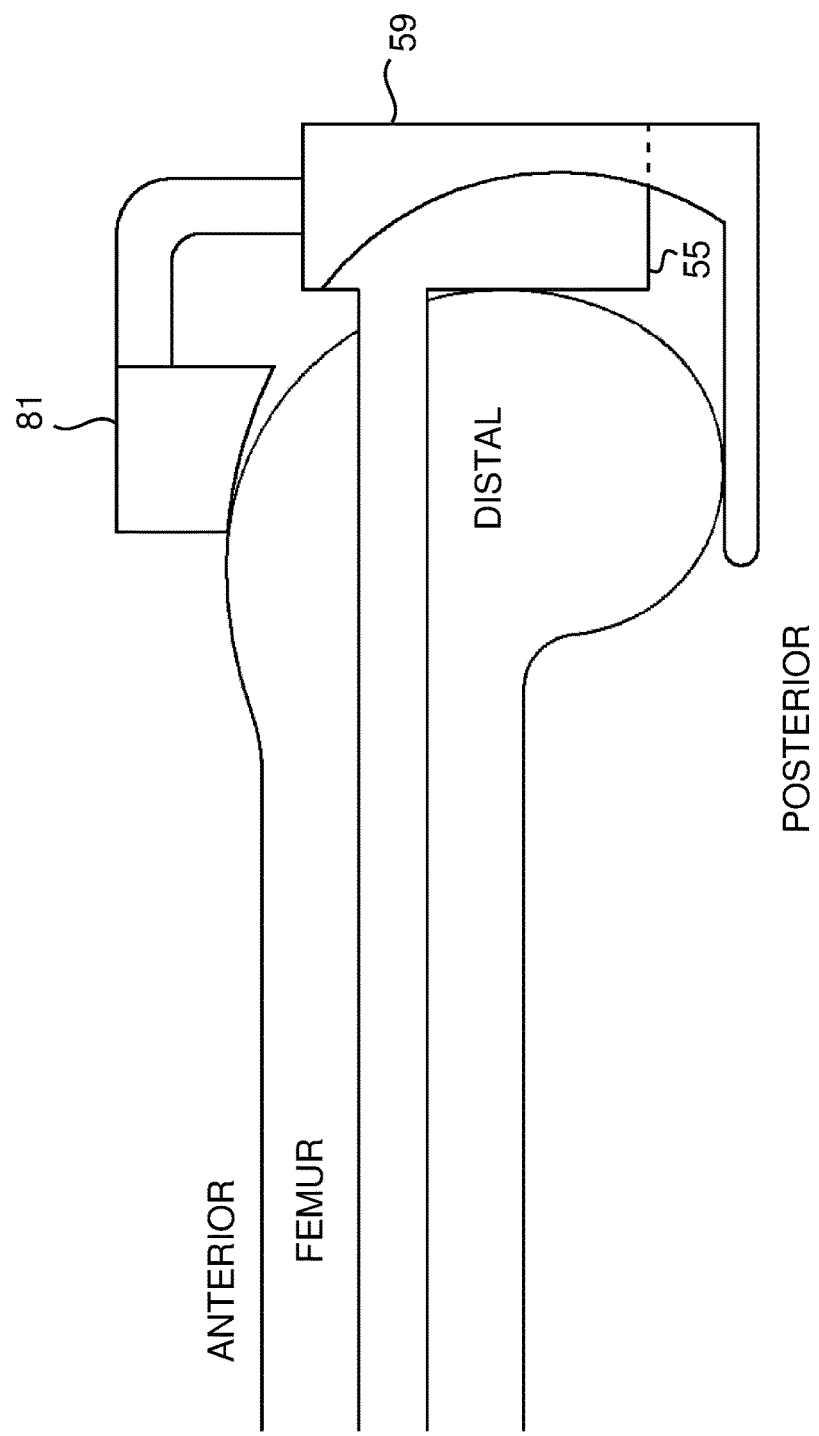
FIGS. 8A and 8B are schematics of a cutting block in standard position and in a rotated position, respectively.
Figure 8B:
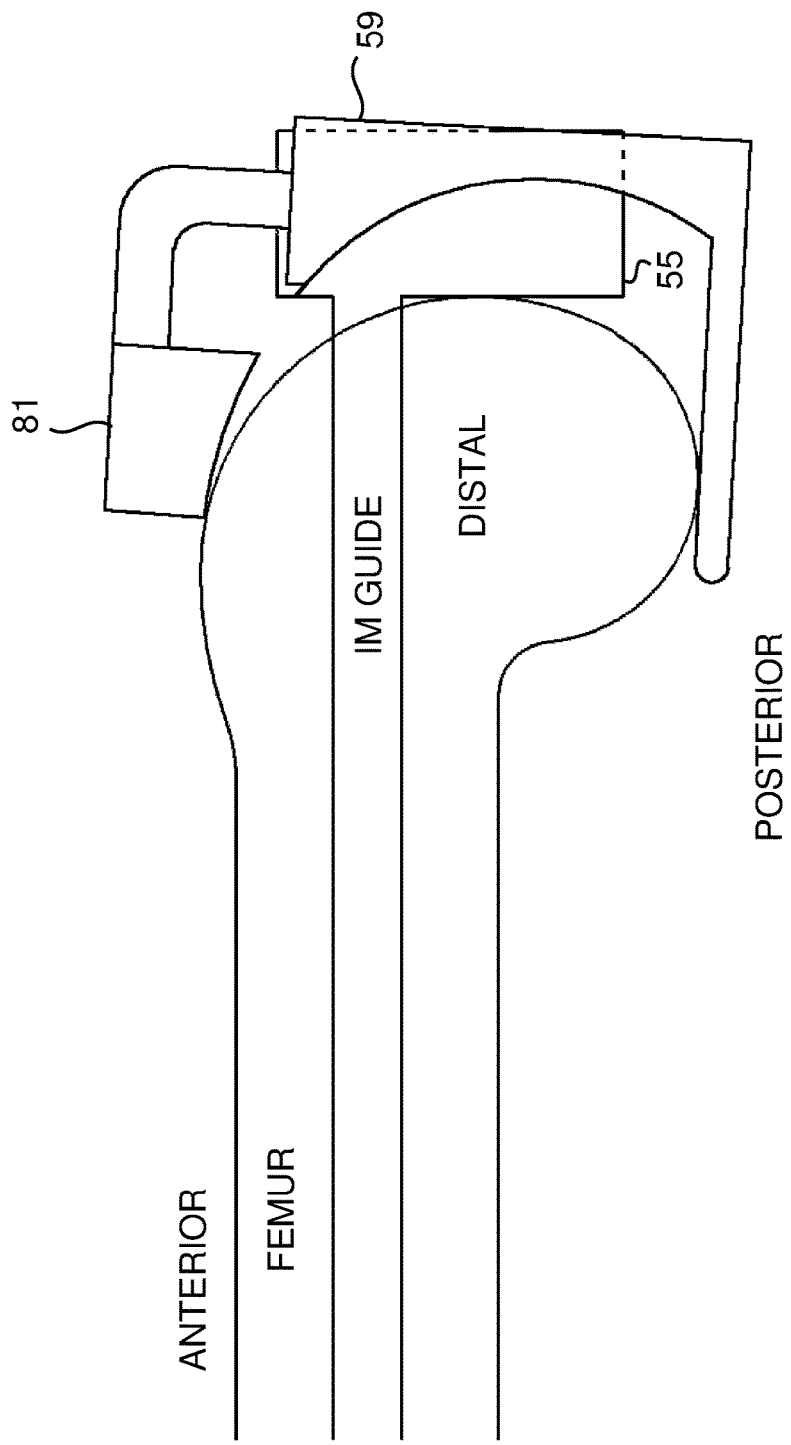

In some embodiments, the adjustable cutting block 81 may simply attach to part of the guide 50, such as the head 55" of the alignment mechanism. In FIG. 8A, the adjustable cutting block 81 is attached to body 59 first in a standard alignment (0 degrees rotation in flexion). In FIG. 8B, the adjustable cutting block has been adjusted to a rotated angle corresponding with the angle determined by the guide 50. In alternative embodiments, the guide 50 may be removed and a suitable adjustable cutting block 81 of the surgeon's choosing may be used for making the distal resection. The remaining resections of the distal femur may be performed according to known methods provided they take into account the rotated angle into flexion of the distal resection.

A number of different devices may be used to control the positioning of the saw blades for performing the resection. Flat metallic blocks on which the saw blade is rested obviously rely to some extent on the skill of the surgeon to avoid tilting of the saw blade, as may happen when the saw encounters a localized harder (sclerotic) section of bone, or when the saw blade has a long travel beyond the guide surface. Slots having small clearance relative to the thickness of the saw blade may also be used. In general these offer better control of the saw blade than open style blocks.

Block type cutting guides are shown in, for example, U.S. Pat. Nos. 4,474,177, 4,487,203, 4,502,483, 4,524,766 and 4,567,885, all of which are incorporated herein by reference.

Fulcrum type cutting guides are described in, for example, U.S. Pat. Nos. 4,718,413 and 4,892,093, both of which are incorporated herein by reference. These consist of an upper and a lower guide surface which are linearly separated along the plane of intended cut by the saw blade. By providing a separation between the two surfaces the saw blade, including its tooth set, may be introduced between the two surfaces and then biased against them to control the cutting plane.

The separation of the guide surfaces normal to the plane of operation of the saw blade is typically matched to the thickness of the saw blade. The choice of orientation of the guide surfaces is chosen so that any deviation by the surgeon in maintenance of the contact between the saw blades and either of the guide surfaces results in conservative removal of bone, which may be subsequently corrected. The guide of U.S. Pat. No. 4,892,093 sits on the already prepared distal femur and provides for the cutting of four additional cuts.

In addition to the exemplary instrumented systems shown in the drawings, in some embodiments a guide 50 or 50' and system may also be electronically instrumented with partial use of computer hardware, software, and/or firmware, pre-operatively adjusting the rotation of the distal femoral cut from the standard 90 degrees and producing a custom distal femoral cutting block that has the patient-specific angle of femoral component rotation built into it.

Figure 10:
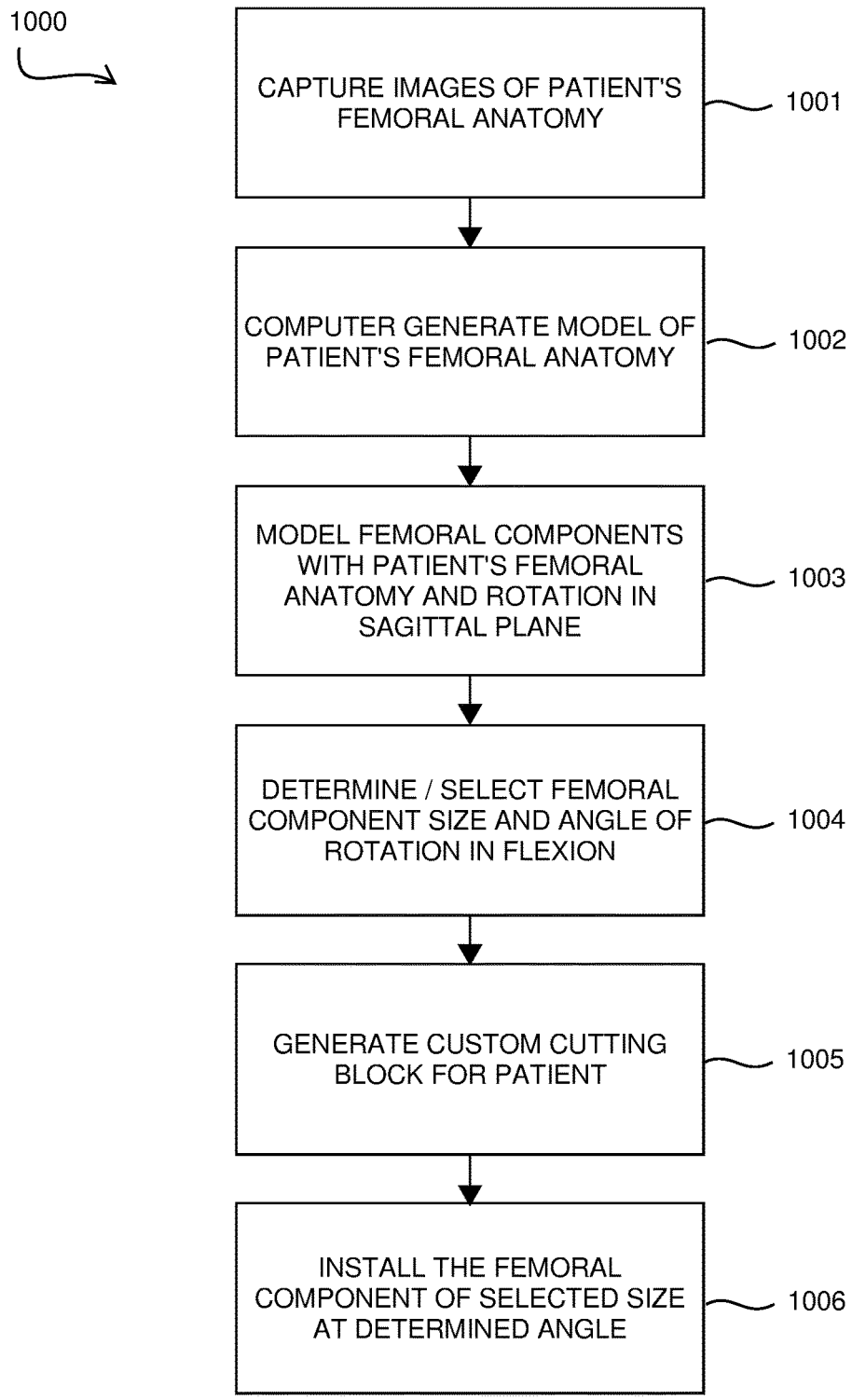
FIG. 10 shows a method for performing knee arthroplasty.

Reference will now be made to FIG. 10 showing a procedure 1000 for performing knee arthroplasty including determining a femoral component size and installation angle for a patient-specific femur. One or more images or imaging data of the patient's femur may first be captured with an imaging device such as, for example, a computed tomography (CT) or magnetic resonance imaging (MRI) machine (block 1001). The images or imaging data generated by the imaging device may be transmitted to a computer or computing system with one or more processors configured or configurable to generate a model of the patient's distal femoral anatomy (block 1002). In an exemplary embodiment, the processors may further model femoral components of available sizes arranged on the patient's modeled femur together with angles of rotation in flexion in the sagittal plane of the femur (block 1003). This modeling may include displaying a two-dimensional or three-dimensional rendering of the patient's femur and a femoral component on a display device such as a monitor or screen. After a determination of a femoral component size and angle of rotation in flexion at which to install the femoral component (block 1004), these items of information may be transferred to a cutting block manufacturing device such as a molding device or a three-dimensional printer. A custom cutting block may then be generated which custom fits the patient's specific femur and includes upon production one or more guide structures or surfaces for guiding a surgeon's resection tool (e.g. saw) to make the distal resection of the patient's femur at the determined angle of rotation in flexion (block 1005). The cutting block is then used in installing the femoral component of the selected size on the specific patient's femur at the determined angle (block 1006).

While exemplary embodiments of the present invention have been disclosed herein, one skilled in the art will recognize that various changes and modifications may be made without departing from the scope of the invention as defined by the following claims.

Having thus described my invention, what I claim as new and desire to secure by Letters Patent is:

1. A guide for determining sizing and positioning of a femoral component for knee arthroplasty of a patient-specific femur that has an anterior surface and a posterior surface, comprising:

an alignment mechanism for aligning said guide with a datum feature of the patient-specific femur, wherein the alignment mechanism is configured to maintain a fixed position relative to the datum feature of the femur in a state of use;

a posterior referencing part configured to contact said posterior surface;

an anterior referencing part configured to contact said anterior surface, said anterior referencing part being displaceable with respect to said posterior referencing part to increase or decrease a spacing therebetween; and a pointer and a plurality of sizing indicia, wherein at least one of said pointer and said plurality of sizing indicia is moveable with respect to the other when said spacing between said posterior and anterior referencing parts increases or decreases, wherein the anterior and posterior referencing parts are configured such that, when one or more of said anterior and posterior referencing parts are rotated in a sagittal plane of said patient-specific femur relative to said alignment mechanism, said anterior and posterior referencing parts respectively maintain contact with said anterior and posterior surfaces, wherein an alignment of said pointer with one indicium of said plurality of sizing indicia determines a femoral component size for said patient-specific femur, and wherein a rotation of said one or more of said anterior and posterior referencing parts relative to said alignment mechanism in the sagittal plane determines an angle relative to said datum feature at which to install a femoral component having said femoral component size on said patient-specific femur.

2. The guide of claim 1, wherein said anterior referencing part is a stylus configured to maintain contact with said anterior surface of said femur and wherein said posterior referencing part is one or more feet configured to maintain contact with one or more posterior surfaces of condyles of said femur.

3. The guide of claim 1, wherein said datum feature with which said alignment guide is configured to align is a femoral longitudinal axis.

4. A guide for determining sizing and positioning of a femoral component for knee arthroplasty of a patient-specific femur that has an anterior surface and a posterior surface, comprising:

an alignment mechanism for aligning said guide with a datum feature of the patient-specific femur, wherein the alignment mechanism is configured to maintain a fixed position relative to the datum feature of the femur in a state of use;

a posterior referencing part configured to contact said posterior surface;

an anterior referencing part configured to contact said anterior surface, said anterior referencing part being displaceable with respect to said posterior referencing part to increase or decrease a spacing therebetween; and an electronic gauge configured to detect a position of said posterior referencing part relative to said anterior referencing part, wherein the anterior and posterior referencing parts are configured such that, when one or more of said anterior and posterior referencing parts are rotated in a sagittal plane of said patient-specific femur relative to said alignment mechanism, said anterior and posterior referencing parts respectively maintain contact with said anterior and posterior surfaces, wherein said electronic gauge determines a femoral component size for said patient-specific femur based on said detected position, and wherein a rotation of said one or more of said anterior and posterior referencing parts relative to said alignment mechanism in the sagittal plane determines an angle relative to said datum feature at which to install a femoral component having said femoral component size on said patient-specific femur.

5. The guide of claim 4, wherein said position of said posterior referencing part relative to said anterior referencing part which said electronic gauge is configured to detect is said spacing between said posterior and anterior referencing parts.

6. The guide of claim 4, wherein said datum feature with which said alignment guide is configured to align is a femoral longitudinal axis.

7. A guide for determining sizing and positioning of a femoral component for knee arthroplasty of a patient-specific femur that has an anterior surface and a posterior surface, comprising:

an alignment mechanism for aligning said guide with a datum feature of the patient-specific femur, wherein the alignment mechanism is configured to maintain a fixed position relative to the datum feature of the femur in a state of use;

a posterior referencing part configured to reference a position of said posterior surface; and an anterior referencing part configured to reference a position of said anterior surface, said anterior referencing part and said posterior referencing part having a variable spacing therebetween, wherein the anterior and posterior referencing parts are configured such that, when one or more of said anterior and posterior referencing parts are rotated in a sagittal plane of said patient-specific femur relative to said alignment mechanism, said anterior and posterior referencing parts respectively maintain reference to the positions of said anterior and posterior surfaces, wherein said spacing between said posterior and anterior referencing parts determines a femoral component size for said patient-specific femur, and wherein a rotation of said one or more of said anterior and posterior referencing parts relative to said alignment mechanism in the sagittal plane determines an angle relative to said datum feature at which to install a femoral component having said femoral component size on said patient-specific femur.

8. The guide of claim 7, further comprising a pointer and a plurality of sizing indicia, wherein at least one of said pointer and said plurality of sizing indicia is moveable with respect to the other when said spacing between said posterior and anterior referencing parts increases or decreases, and wherein an alignment of said pointer with one indicium of said plurality of sizing indicia determines the femoral component size for said patient-specific femur.

9. The guide of claim 7, further comprising an electronic gauge configured to detect said spacing between said posterior referencing part and said anterior referencing part, wherein said electronic gauge determines a femoral component size for said patient-specific femur based on said detected spacing.

10. The guide of claim 7, wherein said anterior referencing part is a stylus configured to maintain reference with said anterior surface of said femur and wherein said posterior referencing part is one or more feet configured to maintain reference with one or more posterior surfaces of condyles of said femur.

11. The guide of claim 10, wherein said stylus is configured to maintain contact with said anterior surface of said femur and wherein said one or more feet are configured to maintain contact with one or more posterior surfaces of condyles of said femur.

12. The guide of claim 7, wherein said datum feature with which said alignment guide is configured to align is a femoral longitudinal axis.

* * * * *